US010555668B2

(12) United States Patent
Fukuhara et al.

(10) Patent No.: US 10,555,668 B2
(45) Date of Patent: Feb. 11, 2020

(54) INFORMATION PROCESSING APPARATUS, CONTROL METHOD FOR AN INFORMATION PROCESSING APPARATUS, AND STORAGE MEDIUM HAVING STORED THEREON AN EXECUTION PROGRAM FOR THE CONTROL METHOD

(71) Applicant: CANON KABUSHIKI KAISHA, Tokyo (JP)

(72) Inventors: Makoto Fukuhara, Yokohama (JP); Hiroki Uchida, Tokyo (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 15/468,322

(22) Filed: Mar. 24, 2017

(65) Prior Publication Data

US 2017/0280993 A1 Oct. 5, 2017

(30) Foreign Application Priority Data

Mar. 29, 2016 (JP) ................................. 2016-065982

(51) Int. Cl.
*A61B 3/14* (2006.01)
*A61B 3/10* (2006.01)
*A61B 3/00* (2006.01)
*A61B 3/12* (2006.01)

(52) U.S. Cl.
CPC ............ *A61B 3/102* (2013.01); *A61B 3/0025* (2013.01); *A61B 3/0041* (2013.01); *A61B 3/1233* (2013.01)

(58) Field of Classification Search
CPC ..... A61B 3/102; A61B 5/0066; A61B 3/0025; A61B 3/14; A61B 3/12; A61B 3/1225; A61B 3/1025; A61B 5/0073; A61B 3/152; A61B 3/113; A61B 3/1233; A61B 3/0058; A61B 3/0041; A61B 1/00172; A61B 3/00; A61B 3/0075; A61B 3/0091; A61B 3/117; A61B 3/15
USPC ................ 351/200, 205, 206, 209–211, 221, 351/243–246
See application file for complete search history.

(56) References Cited

U.S. PATENT DOCUMENTS

| | | | | |
|---|---|---|---|---|
| 8,845,098 | B2 | 9/2014 | Uchida | |
| 9,022,569 | B2 | 5/2015 | Nakahara et al. | |
| 9,042,622 | B2 | 5/2015 | Uchida | |
| 2012/0189184 | A1* | 7/2012 | Matsumoto ............ | A61B 3/102 382/131 |
| 2012/0249953 | A1* | 10/2012 | Ono ....................... | A61B 3/102 351/206 |

(Continued)

Primary Examiner — Brandi N Thomas
(74) *Attorney, Agent, or Firm* — Venable LLP

(57) ABSTRACT

Provided is an information processing apparatus configured to acquire more optical coherence tomographic images in a smaller amount of imaging time while suppressing reduction in longitudinal resolution. The information processing apparatus includes: a sampling unit configured to sample interference light between return light from an object to be inspected which has been scanned with measuring light and reference light corresponding to the measuring light; a data extracting unit configured to partially extract, from an output from the sampling unit, data included in the output at a longer sampling interval than an interval for sampling the interference light by the sampling unit so as to generate a plurality of data sets; and a forming unit configured to form tomographic information on the object to be inspected based on the generated plurality of data sets.

33 Claims, 8 Drawing Sheets

(56) References Cited

U.S. PATENT DOCUMENTS

2014/0228681 A1 8/2014 Jia et al.

* cited by examiner

INFORMATION PROCESSING APPARATUS, CONTROL METHOD FOR AN INFORMATION PROCESSING APPARATUS, AND STORAGE MEDIUM HAVING STORED THEREON AN EXECUTION PROGRAM FOR THE CONTROL METHOD

BACKGROUND

Technical Field

The present disclosure relates to an information processing apparatus configured to process information relating to an image of an object to be inspected, a control method for the information processing apparatus, and a storage medium having stored thereon an execution program for the control method.

Description of the Related Art

As an apparatus for acquiring a tomographic image of an object to be measured, for example, a living body, in a non-destructive and non-invasive manner, an optical coherence tomographic apparatus (hereinafter referred to as "OCT apparatus") has been put into practical use. The OCT apparatus is capable of acquiring a tomographic image of an object to be inspected, for example, a retina in a fundus of an eye, and hence is widely used for ophthalmologic diagnosis of the retina or the like.

The OCT apparatus is configured to cause light reflected from the object to be measured and reference light to interfere with each other, and analyze time dependence or wavenumber dependence of an intensity of the interference light, to thereby acquire a tomographic image. As such OCT apparatus, there are known a time domain OCT apparatus, a spectral domain optical coherence tomography (SD-OCT) apparatus, and a swept source optical coherence tomography (SS-OCT) apparatus. The time domain OCT apparatus is configured to acquire depth information on the object to be measured by changing an optical path length of the reference light through changing of a position of a reference mirror. The SD-OCT apparatus is configured to acquire the depth information through use of light emitted by a broadband light source. The SS-OCT apparatus is configured to acquire the depth information through use of light emitted by a wavelength-sweep light source capable of changing an oscillation wavelength. The SD-OCT apparatus and the SS-OCT apparatus are collectively referred to as "Fourier domain optical coherence tomography (FD-OCT) apparatus".

In recent years, there has been proposed simulated angiography using the FD-OCT apparatus, which is referred to as "OCT angiography (OCTA)". In fluorescein angiography, which is general angiography in contemporary clinical medicine, injection of a fluorescent dye (for example, fluorescein or indocyanine green) into a body is required. A bright region through which the fluorescent dye passes is imaged, to thereby display a vessel two-dimensionally. However, a contrast medium may produce side effects including nausea, eruption, and coughing, and may cause shock symptoms on rare occasions. Hence, fluorescein angiography involves some risks. Meanwhile, OCTA enables non-invasive simulated angiography without the risk of injecting foreign matter into the body, and enables three-dimensional display of a network of vessels. In addition, OCTA is attracting attention because OCTA is higher in resolution than fluorescein angiography and can visualize minute vessels of the fundus.

As OCTA, there are proposed a plurality of methods depending on a difference in manner of detecting a vessel region. For example, in U.S. Patent Application Publication No. 2014/228681, there is proposed a method involving splitting an optical spectrum of interference light into several narrow spectral bands and reducing a longitudinal resolution, to thereby lower sensitivity for motion noise in a depth direction and extract a vessel image with high sensitivity.

In OCTA, the same cross-section is repeatedly imaged, and a difference between signals acquired by the respective imaging operations is extracted, to thereby identify the vessel region. That is, information relating to an image of the same cross-section is processed, to thereby identify an attention region within the image. In this case, a plurality of, at least two, optical coherence tomographic images of the same cross-section are required to generate a cross-sectional image (blood flow information cross-sectional image) for obtaining blood flow information. In addition, in order to enhance the accuracy of the blood flow information, it is effective to obtain more optical coherence tomographic images of the same cross-section.

For example, a tomographic image of a retina is generally acquired under a state in which a subject to be examined fixes his or her line of sight on one point (fixation), but it becomes more difficult to obtain an image with a stable fixation state as an imaging time becomes longer. The fixation performed for a long time also imposes a burden on the subject to be examined, and hence it is difficult to accept the fixation performed for a long time from this viewpoint as well. Therefore, it is desired that more optical coherence tomographic images be acquired for a smaller amount of imaging time.

The apparatus disclosed in U.S. Patent Application Publication No. 2014/228681 is configured to scan the same cross-section a plurality of times, to split an interference spectrum into M spectral bands, and to generate optical coherence cross-sectional images from the respective spectral bands obtained through the division. Then, a correlation value between the cross-sectional images obtained by being increased through splitting is obtained, to thereby obtain the blood flow information having high accuracy. However, the longitudinal resolution is reduced by dividing an OCT interference signal into the M spectral bands, and hence the blood flow information cross-sectional image cannot be generated at high resolution.

Further, not only when the blood flow information cross-sectional image is generated but also when averaging is performed on a plurality of optical coherence tomographic images, it is required to acquire more optical coherence tomographic images in a smaller amount of imaging time while suppressing reduction in longitudinal resolution.

SUMMARY

In view of the above, the present disclosure has an object to process image information so as to acquire more optical coherence tomographic images in a smaller amount of imaging time while suppressing reduction in longitudinal resolution.

In order to solve the above-mentioned problem, according to one embodiment of the present disclosure, there is provided an information processing apparatus, including:

a sampling unit configured to sample interference light between return light from an object to be inspected which has been scanned with measuring light and reference light corresponding to the measuring light;

a data extracting unit configured to partially extract, from an output from the sampling unit, data included in the output at a longer sampling interval than an interval for sampling the interference light by the sampling unit so as to generate a plurality of data sets; and a forming unit configured to form tomographic information on the object to be inspected based on the generated plurality of data sets.

According to the present disclosure, more optical coherence tomographic images can be acquired in a smaller amount of imaging time while suppressing reduction in longitudinal resolution.

Further features of the present invention will become apparent from the following description of exemplary embodiments with reference to the attached drawings.

DESCRIPTION OF THE EMBODIMENTS

[Entire Configuration of Imaging Apparatus]

Now, with reference to the accompanying drawings, an embodiment of the present disclosure is described in detail. The embodiment described below does not intend to limit the present disclosure relating to the appended claims. Not all combinations of features described in the following embodiment are necessarily essential to solutions of the present disclosure.

Figure 1:
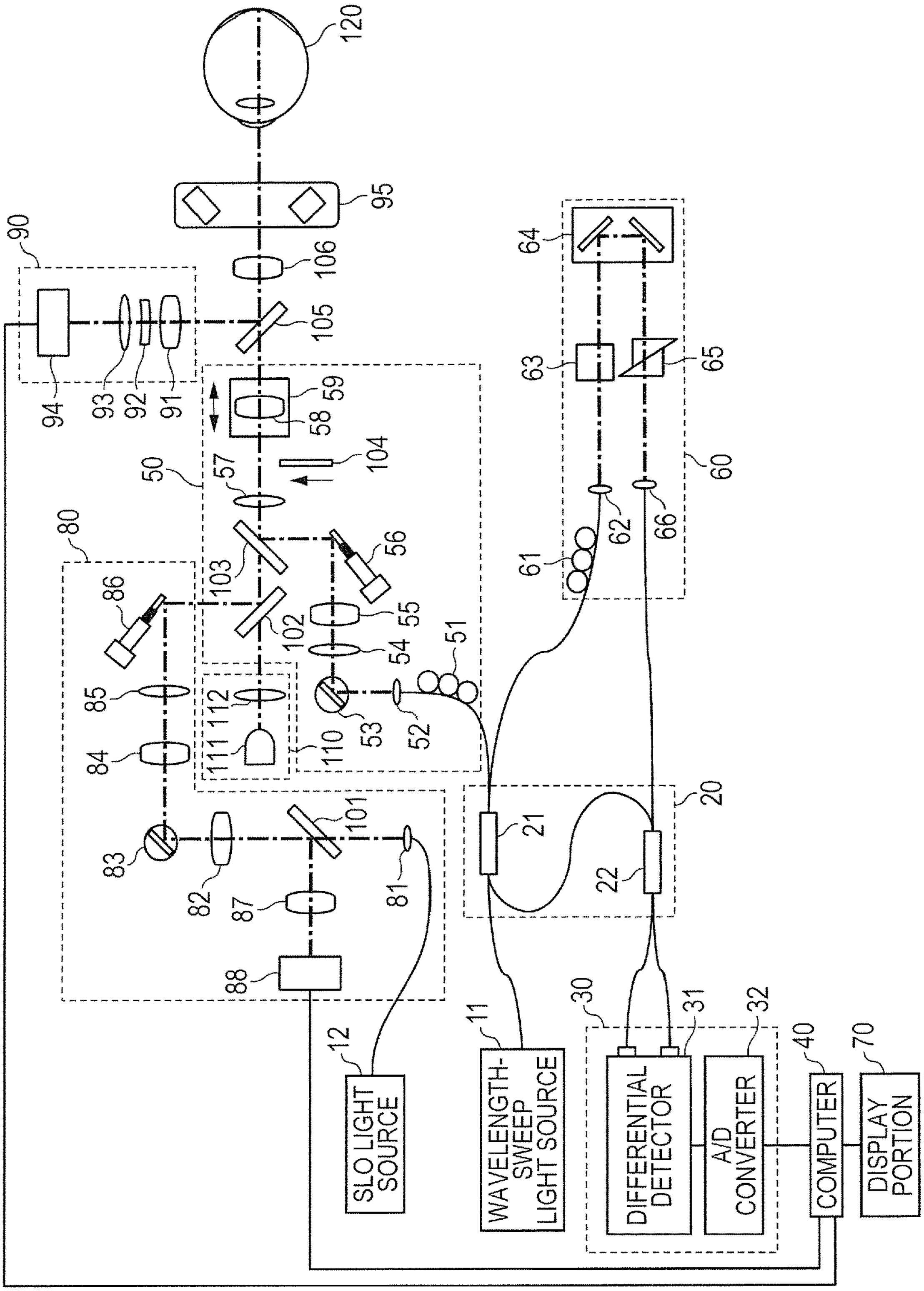
FIG. 1 is a schematic diagram of an entire configuration of an imaging apparatus according to one embodiment of the present disclosure.

FIG. 1 is a schematic diagram of a configuration example of an information processing apparatus including an imaging apparatus (OCT apparatus) using optical coherence tomography according to one embodiment of the present disclosure. Examples of an apparatus used for OCTA (OCT apparatus) include the SD-OCT apparatus and the SS-OCT apparatus that are described above. The description of this embodiment is directed to a configuration using the SS-OCT apparatus. In the SS-OCT apparatus, a swept source type capable of sweeping a wavelength of output light over time is used to sample interference light at an equal wavenumber interval based on a sample clock output by a clock generating unit described later.

The OCT apparatus according to this embodiment includes a wavelength-sweep light source 11 configured to emit light having an optical frequency to be swept, an OCT interference portion 20 configured to generate interference light, and a detector portion 30 configured to detect the interference light. The OCT apparatus is connected to a computer 40 configured to acquire and process image information on a fundus of an eye to be inspected 120 detected by the detector portion 30 based on the interference light, to thereby form the information processing apparatus. The OCT apparatus further includes a measurement arm 50 and a reference arm 60. The wavelength-sweep light source 11 emits light to be split into measuring light and reference light, which are described later.

Further, the OCT apparatus includes an anterior ocular segment imaging portion 90 and an SLO optical system forming a scanning laser ophthalmoscope (hereinafter referred to as "SLO"). The SLO is used to obtain a fundus image to be used for the grasp or designation of an imaging range to be used by the OCT apparatus, an imaging range to be used by OCTA, or the like, and includes an SLO light source 12 for illumination light, which is used to obtain reflected light from the fundus. The anterior ocular segment imaging portion 90 is used to acquire an image for alignment between an OCT measuring system of the OCT apparatus, which is described later, and the eye to be inspected 120, or other such purpose.

<Configuration of OCT Measuring System>

The OCT interference portion 20 includes couplers 21 and 22. The coupler 21 is connected to each of the wavelength-sweep light source 11, the coupler 22, the measurement arm 50, and the reference arm 60 through an optical fiber. The reference arm 60 and the coupler 22 are also connected to each other through an optical fiber as described later. First, the coupler 21 splits the light emitted from the wavelength-sweep light source 11 and guided by the optical fiber into the measuring light to irradiate the fundus of the eye to be inspected 120 and the reference light. In this embodiment, a split ratio of light is set to (measuring light):(reference light)=2:8. The measuring light passes through the measurement arm 50 described later to irradiate the fundus of the eye to be inspected 120.

More specifically, the measuring light guided from the coupler 21 to the measurement arm 50 through the optical fiber has a polarization state adjusted by a polarization controller 51 provided to the optical fiber, and is then emitted from a collimator lens 52 as spatial light. After that, the measuring light passes through an X scanner 53, lenses 54 and 55, a Y scanner 56, a dichroic mirror 103, a lens 57, a focus lens 58, a dichroic mirror 105, and an objective lens 106 to irradiate the fundus of the eye to be inspected 120. The focus lens 58 is fixed on a focus stage 59, and is configured to move in an optical axis direction indicated by the arrows in FIG. 1 by the focus stage 59. The movement of the focus lens 58 enables the measuring light to achieve an in-focus state on the fundus.

The X scanner 53 and the Y scanner 56 are each a scanning portion having a function of scanning the fundus with the measuring light. A radiating position of the measuring light with respect to the fundus is changed by the scanning portions, and the imaging range on the fundus is scanned with the measuring light by continuously changing the radiating position. The dichroic mirror 103 has a characteristic of reflecting light having a wavelength of from 1,000 nm to 1,100 nm and transmitting light having another wavelength. Therefore, the measuring light is reflected toward the eye to be inspected 120 by the dichroic mirror 103, and the other light, for example, the illumination light of SLO, is transmitted through the dichroic mirror 103.

Backward scattered light (reflected light) of the measuring light from the fundus travels backward on the above-mentioned optical path to be guided to the optical fiber by the collimator lens 52 and guided from the measurement arm 50 to the coupler 21 through the optical fiber. Return light of the measuring light from the eye to be inspected 120 further passes through the coupler 21 to be guided to the coupler 22 through the optical fiber. Based on the above-mentioned split ratio, 80% of the return light from the fundus is guided to the coupler 22.

Meanwhile, the reference light guided from the coupler 21 to the reference arm 60 through the optical fiber further passes through the reference arm 60 to enter the coupler 22 through the optical fiber connecting the reference arm 60 and the coupler 22 to each other. More specifically, the reference light guided from the coupler 21 to the reference arm 60 through the optical fiber has the polarization state adjusted by a polarization controller 61, and is then emitted from a collimator 62 as spatial light. After that, the reference light passes through a dispersion compensation glass 63, an optical path length adjustment optical system 64, a dispersion adjustment prism pair 65, and a collimator lens 66 to enter the optical fiber. By passing through those optical members, the reference light has dispersion, an optical path length, and the like matching those of the measuring light. The reference light passing through the reference arm 60 is guided to the coupler 22 by the optical fiber in the above-mentioned manner.

The coupler 22 functions as a combining unit configured to cause the return light from the eye to be inspected 120, which has passed through the measurement arm 50, to interfere with the reference light that has passed through the reference arm 60, and is configured to generate interference light (combined light). The interference light is sampled by the detector portion 30 as output light from the combining unit. The detector portion 30 includes a differential detector 31 and an A/D converter 32. More specifically, the interference light combined and generated by the coupler 22 is split by the coupler 22. Respective light beams obtained through the splitting by the coupler 22 are guided to the differential detector 31, that is, the detector portion 30 through the corresponding optical fibers. The differential detector 31 generates an interference signal from the respective light beams obtained through the splitting.

The interference signal obtained by converting the interference light into an electrical signal by the differential detector 31 is sampled by the A/D converter 32, and is further converted into a digital signal. In this case, in the OCT apparatus (detector portion 30) illustrated in FIG. 1, the interference light is sampled at an equal optical frequency interval (equal wavenumber interval) based on a k-clock signal generated by a k-clock generating portion built into the wavelength-sweep light source 11. In this embodiment, the digital signal (output from a sampling unit) output from the A/D converter 32 within the detector portion 30 functioning as the sampling unit is sent to the computer 40.

The functions of the respective components involved in the above description of the configuration of the OCT apparatus serve as a process of acquiring information relating to a cross-section at one given point on the fundus of the eye to be inspected 120. Measuring light scanning of thus radiating the measuring light to one point on an object to be inspected exemplified by the fundus of the eye to be inspected 120 to acquire the information relating to the cross-section in its depth direction is referred to as "A scan". Further, measuring light scanning for acquiring information relating to a cross-section of the object to be inspected along a scanning plane in one direction, which is a direction orthogonal to the A scan, that is, a 2-D image regarding a plane formed of the one direction and the depth direction is referred to as "B scan". In addition, measuring light scanning in another direction in the scanning plane of the object to be inspected orthogonal to both scanning directions for the A scan and the B scan is referred to as "C scan".

In this embodiment, when the measuring light is two-dimensionally raster-scanned on the fundus in order to acquire a three-dimensional tomographic image of the fundus, high-speed scanning is performed in the B scan direction. Further, low-speed scanning is performed in the C scan direction in order to scan the measuring light such that the scanning lines of the B scan are aligned in a direction orthogonal to the B scan direction. A two-dimensional tomographic image can be obtained by performing the A scan and the B scan, and a three-dimensional tomographic image can be obtained by performing the A scan, the B scan, and the C scan. The B scan and the C scan are performed by operating the X scanner 53 and the Y scanner 56, respectively, which are described above.

The X scanner 53 and the Y scanner 56 are formed of deflecting mirrors arranged so as to have their respective rotary axes orthogonal to each other. The X scanner 53 is configured to perform scanning in the X-axis direction through use of the measuring light, and the Y scanner 56 is configured to perform scanning in the Y-axis direction through use of the measuring light. The respective directions of the X-axis direction and the Y-axis direction are directions orthogonal to the direction of an ocular axis of an eyeball and orthogonal to each other. Further, such directions of line scanning as the B scan direction and the C scan direction may not necessarily match the X-axis direction and the Y-axis direction. Therefore, the directions for the line scanning of the B scan and the C scan can be determined appropriately depending on a 2-D tomographic image or a 3-D tomographic image to be acquired.

The description of this embodiment is directed to the case of using the SS-OCT apparatus, but the SS-OCT apparatus may be replaced by the SD-OCT apparatus as described above. As described later, in this embodiment, from among outputs obtained by sampling the interference signal, outputs obtained at a fixed timing longer than the timing of the sampling are extracted. That is, outputs obtained at a fixed wavenumber interval are extracted from among outputs obtained at equal wavenumber intervals, and a blood flow information cross-sectional image is obtained based on the extracted outputs. In the SD-OCT apparatus, a spectroscopic unit is configured to separate light within a measuring band into spectral components as separated light. The respective light beams of the separated light are received by a plurality of light-receiving elements arranged in line, and each of the light-receiving elements receives a light beam having a corresponding wavenumber to obtain intensity information on the interference light. That is, the interference light is sampled at an equal wavenumber interval through the arrangement of the light-receiving elements. Therefore, when the SD-OCT apparatus is used in place of the SS-OCT apparatus, it is possible to obtain an effect equivalent to that of this embodiment through use of outputs from specific sensors arranged at an arbitrary interval selectively from among a plurality of sensors that are arranged.

<Configuration of SLO Measuring System>

The illumination light emitted from the SLO light source 12 is radiated on the fundus of the eye to be inspected 120 through the SLO optical system 80. More specifically, light that has entered the SLO optical system 80 is emitted from a collimator lens 81 to space as collimated light. After that, the light passes through a hole portion of a holed mirror 101, a lens 82, an X scanner 83, lenses 84 and 85, and a Y scanner 86 to reach a dichroic mirror 102. The X scanner 83 and the Y scanner 86 are merely an example of scanning units for SLO, and the X scanner 53 and the Y scanner 56 for OCT may be used as the scanning units for SLO. The dichroic mirror 102 has a characteristic of reflecting light having a wavelength of from 760 nm to 800 nm and transmitting light having another wavelength. The illumination light reflected by the dichroic mirror 102 passes through the dichroic mirror 103, and follows the same optical path as that of the OCT measuring system to reach the fundus of the eye to be inspected 120.

The illumination light irradiating the fundus is reflected or scattered by the fundus, and travels backward on a part of the above-mentioned optical path of the OCT measuring system and the optical path of the SLO optical system 80 to return to the holed mirror 101. The illumination light that has reached the eye to be inspected 120 and been reflected by the holed mirror 101 passes through a lens 87, and is received by an avalanche photodiode (hereinafter referred to as "APD") 88. The APD 88 is configured to convert the received light into an electrical signal, and to output the electrical signal to the computer 40. The position of the holed mirror 101 is conjugate with a pupil position of an eye to be inspected. With such an arrangement, a light beam that has passed through a portion around a pupil is reflected by the holed mirror 101 selectively from among the light beams obtained by reflecting or scattering the illumination light irradiating the fundus.

<Configuration of Anterior Ocular Segment Measuring System>

The anterior ocular segment imaging portion 90 causes an illumination light source 95 formed of an LED configured to emit illumination light having a wavelength of 860 nm to illuminate an anterior ocular segment of the eye. The illumination light reflected by the anterior ocular segment passes through the objective lens 106 to reach the dichroic mirror 105. The dichroic mirror 105 has a characteristic of reflecting light having a wavelength of from 820 nm to 920 nm and transmitting light having another wavelength. The reflected light that has been reflected by the anterior ocular segment and reflected by the dichroic mirror 105 passes through lenses 91, 92, and 93, and is received by an anterior ocular segment camera 94. The reflected light received by the anterior ocular segment camera 94 is converted into an electrical signal, and the electrical signal is output to the computer 40.

<Internal Fixation Lamp 110>

An internal fixation lamp 110 includes a display portion 111 for an internal fixation lamp and a lens 112. In this embodiment, the display portion 111 for the internal fixation lamp is obtained by arranging a plurality of light emitting diodes (LEDs) in a matrix shape. A light emission position of the light emitting diodes is changed depending on a region on the fundus to be imaged. The light from the display portion 111 for the internal fixation lamp is guided to the eye to be inspected 120 through the lens 112. The light emitted from the display portion 111 for the internal fixation lamp has a wavelength of 520 nm, and is configured to display a desired set pattern. A subject to be examined fixes his or her eye on the pattern, which promotes fixation of the eye to be inspected 120. The position of the fixation is changed by changing the display position of the pattern, which enables the imaging of the fundus at an arbitrary position.

<Control Portion>

In this embodiment, the computer 40 functions as a control portion. In more detail, the computer 40 is configured to control the respective components of the OCT apparatus to perform a signal process on the above-mentioned various output signals including the interference signal converted into the digital signal, to generate an optical coherence tomographic image and the blood flow information cross-sectional image. Specifically, the computer 40 processes the output signal of SLO converted into the digital signal and sent from the APD 88 to generate an SLO image. The computer 40 further processes the output signal sent from the anterior ocular segment camera 94 to generate an anterior ocular segment image. In addition, those pieces of information on the fundus and the anterior ocular segment obtained as a result of the signal process are displayed by the display portion 70 controlled by the computer 40. Specific details of the signal process for the interference signal and the like, which is performed by the computer 40, are described later in the section "Signal Process Procedure".

As described above, the OCT apparatus being the imaging apparatus according to this embodiment includes, as its main components, the coupler 21, the X scanner 53 and the Y scanner 56, the coupler 22, the detector portion 30, and the computer 40. In this embodiment, those components function as a light splitting unit, the scanning unit, the combining unit, the sampling unit, and a forming unit, respectively. The light splitting unit is configured to split light from the wavelength-sweep light source 11 being the light source into the measuring light to be radiated on the eye to be inspected 120 being the object to be inspected and the reference light corresponding to the measuring light. The scanning unit is configured to scan the fundus of the eye to be inspected 120 with the measuring light. The combining unit is configured to combine the return light from the fundus scanned with the measuring light and the reference light. The sampling unit is configured to sample the output light from the combining unit. The forming unit is configured to form tomographic information on the eye to be inspected 120 based on a data set output from the sampling unit based on the output light.

[Setting of Scan Area]

Figure 2A:
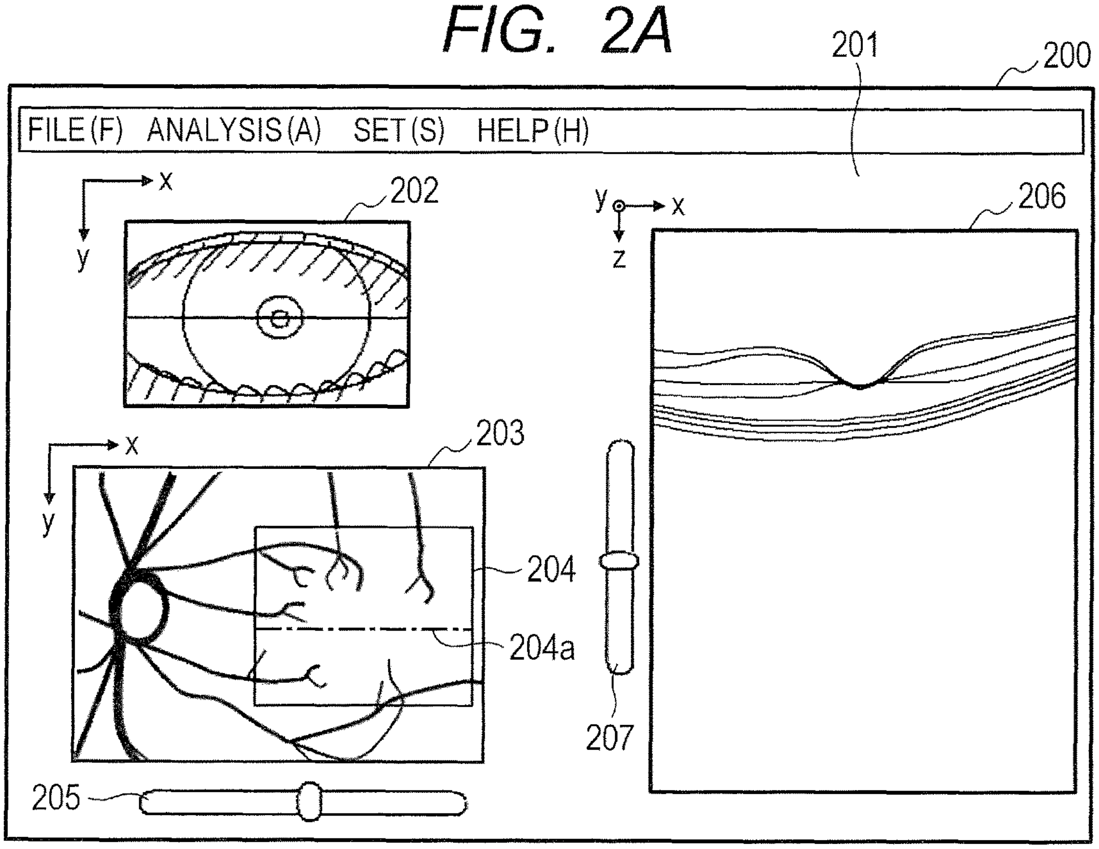
FIG. 2A is a diagram for illustrating an example of an imaging screen according to this embodiment.
Figure 2B:
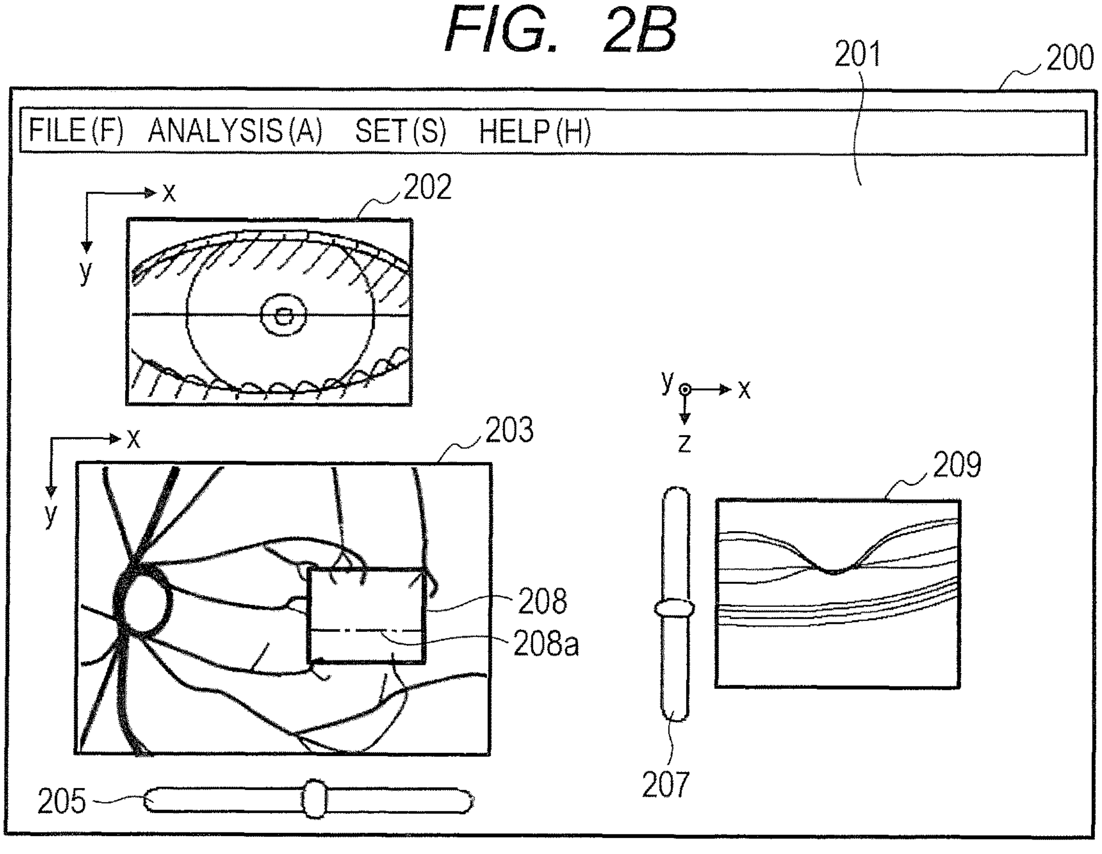
FIG. 2B is a diagram for illustrating another example of an imaging screen according to this embodiment.

FIG. 2A is an illustration of an imaging screen 200 in an OCT mode for obtaining an OCT intensity image, which is to be displayed on the display portion 70 at a time of the imaging. FIG. 2B is an illustration of the imaging screen 200 in an OCTA mode for obtaining the blood flow information cross-sectional image by OCTA. On the imaging screen 200 in the OCT mode illustrated in FIG. 2A, an anterior ocular segment image 202, an SLO fundus image 203, and an optical coherence tomographic image (OCT intensity image) 206, which are generated by the computer 40, are displayed in a display region 201. In the OCTA mode illustrated in FIG. 2B, an optical coherence tomographic image (blood flow information cross-sectional image) 209 is displayed in place of the optical coherence tomographic image 206.

As described above, in OCTA, the intensity information on the same cross-section of the fundus needs to be obtained a plurality of times, and hence the scanning is required to be performed on the same B scan line with the measuring light a plurality of times. However, as has already been discussed, it is not desired that an imaging time be extended, which requires reduction of a length of the B scan line and a scan area on the fundus. Further, an imaging depth range (depth direction range for obtaining an image) within a retina for which a state of a blood flow is to be grasped in actuality is a part of each layer of the retina, and is generally narrower than a range for generating an intensity image acquired by the OCT apparatus. Therefore, the OCT mode for obtaining the intensity image and the OCTA mode for obtaining the blood flow information cross-sectional image may be switched to sample the interference signal.

Now, description is given of an example of a procedure for setting the scan area in the OCT mode or the OCTA mode. First, in the OCT mode, the OCT optical system is aligned with respect to the eye to be inspected 120 based on the anterior ocular segment image 202 illustrated in FIG. 2A. Specifically, for example, the alignment is performed by operating a driving system (not shown) and moving the OCT optical system so that the center of the pupil displayed on the anterior ocular segment image 202 is located on an optical axis of the measuring light within the OCT optical system. The alignment may be manually performed by an examiner, or the computer 40 may automatically perform the alignment while recognizing the anterior ocular segment image 202. Subsequently, in order to clearly display the SLO fundus image 203, the focus lens 58 is moved toward the optical axis direction to perform focus adjustment. The focus adjustment may be manually performed by the examiner through use of a focus adjustment slider 205 displayed on the imaging screen 200, or may be automatically performed by the computer 40 based on the SLO fundus image 203.

When the SLO fundus image 203 is displayed, the scan area of the OCT apparatus on the fundus is designated through use of the image. The OCT scan area can be designated by, for example, a guide 204 displayed on the SLO fundus image 203. For the guide 204, an arbitrary size, an arbitrary shape, and an arbitrary position can be set, and a rectangle of (6 mm)×(6 mm), a radial pattern inscribed in a circle having a diameter of 5 mm, or a line pattern of 16 mm, or the like can be selected. After the OCT scan area is designated by the guide 204, the acquisition of three-dimensional intensity data within the designated scan area is executed by the OCT apparatus. Further, an intensity image of a fundus cross-section within a large or wide imaging depth range at an arbitrary position within the scan area, in this embodiment, at a cross-sectional image acquisition position 204*a*, is displayed as the optical coherence tomographic image 206 based on the acquired three-dimensional intensity data. Finally, a coherence gate is adjusted so as to bring the optical coherence tomographic image 206 into a display state suitable for diagnosis or the like. The adjustment of the coherence gate may be manually performed by the examiner through use of a gate adjustment slider 207, or may be automatically performed by the computer 40 based on the optical coherence tomographic image 206.

The OCTA mode is different from the OCT mode only in the setting of the scan area. That is, in the OCTA mode, as illustrated in FIG. 2B, an OCTA scan area is newly designated in the SLO fundus image 203 through use of an OCTA guide 208. The OCTA guide 208 can be variously changed in shape in the same manner as the above-mentioned guide 204. After the OCTA scan area is designated by the OCTA guide 208, three-dimensional motion contrast data for OCTA within the designated scan area is acquired.

In this embodiment, in order to generate three-dimensional blood flow information for OCTA, it is necessary to calculate the above-mentioned motion contrast data. In this case, the motion contrast is defined as a contrast between a tissue involving flowing (for example, blood) and a tissue involving no flowing among tissues of the object to be inspected. Data including a characteristic amount or the like that expresses the motion contrast is defined as motion contrast data or a motion contrast characteristic amount. The motion contrast characteristic amount is described later in detail.

Further, the optical coherence tomographic image 209 or the blood flow information cross-sectional image of the fundus cross-section within a small or narrow imaging depth range at an arbitrary position within the scan area, in this embodiment, at a cross-sectional image acquisition position 208*a* is displayed based on the acquired two-dimensional motion contrast data. Finally, the coherence gate is adjusted so that the optical coherence tomographic image 209 becomes optimal. The adjustment of the coherence gate may be manually performed by the examiner through the use of the gate adjustment slider 207, or may be automatically performed by the computer 40 based on the optical coherence tomographic image 209.

The case where the three-dimensional intensity data for OCT and the three-dimensional motion contrast data for OCTA are separately acquired has been described above. However, those pieces of data may be acquired simultaneously. In this case, the guide 204 and the OCTA guide 208 match each other. Specifically, the above-mentioned motion contrast data is data obtained by extracting a part that has caused time modulation in individual pixel values obtained from the same cross-section at different times by the OCT apparatus.

As described later, in this embodiment, from the viewpoint of extracting the data set, when the interference signal is sampled in the OCTA mode, the depth direction range required for the interference signal to be sampled needs to be at least two times as wide as a depth range of a tomographic image to be displayed in actuality. Therefore, in this embodiment, in the OCTA mode, the size of the scan area can be set smaller than in the OCT mode, but it is preferred that the depth direction range be equivalent to the case of the OCT mode. That is, the depth direction range displayed as the blood flow information cross-sectional image becomes smaller or narrower than the depth direction range used in actual measurement for OCTA.

[Scan Pattern]

Figure 3:
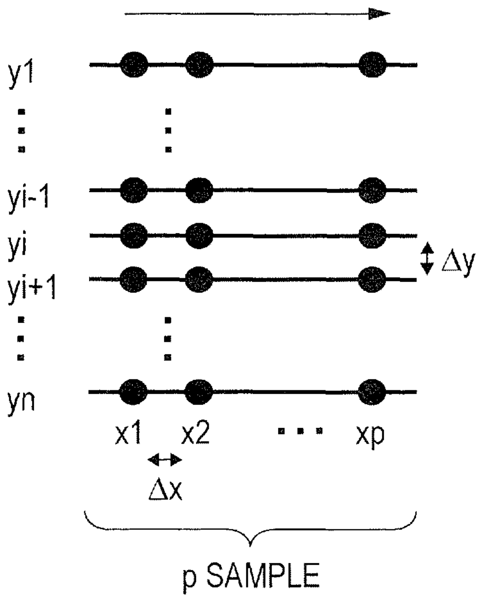
FIG. 3 is a diagram for illustrating a mode of scanning measuring light according to this embodiment.

Next, a scan pattern of the measuring light according to this embodiment is described with reference to FIG. 3. In OCTA, in order to measure the change with time of the interference signal due to the blood flow, measurement is required to be performed a plurality of times at the same position. In this embodiment, in OCTA, scanning of repeating the B scan at the same position m times and moving to n Y-positions is performed. A specific scan pattern is illustrated in FIG. 3. At each of the n Y-positions of y1 to yn on the fundus plane, the scanning is performed m times by repeating the B scan m times.

In order to correctly measure the change with time of the interference signal, those m times of B scan are required to be performed at the same position on the fundus. However, the eye to be inspected always performs involuntary eye movement during fixation, and hence the measuring light scanning at the same position is in reality not easy even when scanning is intended on the same scanning line. The measuring light scanning that is performed with the intention to B scan the measuring light on the same-position scanning line is herein referred to as scanning the measuring light on the same scanning line. Further, it is conceivable to execute the B scan a plurality of times while slightly shifting the scanning line intentionally, and perform averaging or other processes the obtained interference signals regarding pixels corresponding thereto, to thereby reduce noise. In this case, those substantially equal scanning lines of the measuring light are expressed as the same scanning line, and further, the tomographic image obtained through the averaging or other processes is also expressed as the tomographic image obtained from the same scanning line. The averaging is executed by the computer 40 functioning as an arithmetic operation unit configured to average the respective pixel values for the generated plurality of tomographic images.

As the value of m, which is the number of repetition times, becomes larger, the number of measurement times at the same position also increases, and hence an accuracy of detecting the blood flow increases. Meanwhile, the scan time of the measuring light increases, and hence there arise fears that a motion artifact occurs in an image due to the above-mentioned movement of an eye (involuntary eye movement during fixation) during a scan and that burden on the subject to be examined increases. In this embodiment, m is determined as 3 in consideration of the balance between the measurement time and the detection accuracy. The number of repetition times m may be freely changed depending on an A scan speed of the OCT apparatus or a movement amount of the eye to be inspected 120.

In FIG. 3, p represents the number of samples of the A scan in one B scan. In other words, the size of the plane image is determined based on p×n. As p×n increases, a wider range can be scanned as long as a measurement pitch is the same. However, the scan time increases, and hence the above-mentioned motion artifact and increase in the burden on the subject to be examined are required to be taken into consideration.

Further, Δx of FIG. 3 is an interval (x-pitch) between A scan positions (X-positions) adjacent on the same B scan line, and Δy of FIG. 3 is an interval (y-pitch) between adjacent B scan lines (Y-positions). In this embodiment, the x-pitch is determined as ½ of a beam spot diameter of the measuring light on the fundus, and is set to 10 μm. Even when the pitch is set smaller than ½ of the beam spot diameter on the fundus, an effect of increasing the definition of the image to be generated is small. In the same manner as Δx, Δy is set to 10 μm. In order to reduce the scan time, Δy may be set larger than 10 μm within a range that does not exceed 20 μm being the beam spot diameter.

In regard to the x-pitch and the y-pitch, when the beam spot diameter on the fundus is set larger, the definition deteriorates, but a wide-range image can be acquired with a small data volume. Therefore, the x-pitch and the y-pitch may be changed freely depending on clinical demands.

In the fundus of an average adult, a distance between a macula and an optic papilla on the retina is about 14 mm. The measuring light is used to scan the fundus with a pupil center of the eye to be inspected 120 as a fulcrum. Therefore, in consideration of 24 mm being an average diameter of an eyeball of an adult male and 1.38 being an average refractive index inside the eyeball, in order to contain the macula and the optic papilla on the same screen, a scan angle range therefor is $\arcsin(1.38\times\sin(33.4°/2))\approx 47°$. In other words, in a case where the fundus is linearly scanned with the measuring light, that is, in a case where the object to be inspected is scanned with the measuring light, the above-mentioned tomographic image including both the tissues is obtained when the air-converted scan angle range is equal to or larger than 47°.

Further, in the case of OCT for fundus inspection, a retina to be inspected has a thickness of 0.50 mm at the thickest part, and a choroid has a thickness of about 0.30 mm. In the eye to be inspected, a distance from the fulcrum of the measuring light to the deepest portion of the fundus and a distance from the fulcrum to a fundus position near the maximum angle of the scan angle range are different from each other, and a difference of about 1.2 mm exists in a model eye having an average size. Therefore, for example, in order to obtain interference signals of from the front surface of the retina to a depth-side boundary of the choroid in consideration of the difference between the two distances in the model eye or the like, it is required to obtain information having a depth of $2\times(0.5+0.3+1.2)=4.0$ mm as the depth direction range. Therefore, it is preferred that the tomographic image having a large imaging depth range illustrated in FIG. 2A or FIG. 2B correspond to, for example, a tomographic image having a depth range equal to or larger than 4.0 mm, and that the tomographic image having a small imaging depth range correspond to a tomographic image having a depth range smaller than 4.0 mm (or equal to or smaller than 4.0 mm).

In this embodiment, the computer 40 includes an input unit (not shown) capable of receiving input of an instruction from the outside. The examiner can input the scan angle range and the depth direction range for obtaining the interference signal in OCT through the input unit formed of, for example, a combination of a GUI and a mouse. The computer 40 further functions as an imaging range setting unit configured to set a predetermined range of the fundus to be scanned with the measuring light in a two-dimensional scan pattern formed of a predetermined number of scan lines for the scanning unit based on such an input instruction. In consideration of the above-mentioned various dimensions of the general eye, it is preferred that a plurality of data sets extracted for generating the tomographic image having a small imaging depth range be based on the output light obtained under a condition that the scan angle range of the measuring light used by the scanning unit is smaller than 47°. In another case, it is preferred that a data extracting unit extract the plurality of data sets for generating the tomographic image having a small imaging depth range when the scan angle range of the measuring light used by the scanning unit is smaller than 47°. In another case, it is preferred that the imaging range setting unit be able to switch the scan angle range of the measuring light used by the scanning unit between a first imaging range equal to or larger than 47° and a second imaging range smaller than 47°. In this case, it is further preferred that the detector portion 30 obtain the tomographic information having an imaging depth range equal to or larger than 4.0 mm inside the eyeball of the eye to be inspected 120.

[Procedure for Acquiring Interference Signal]

Figure 4:
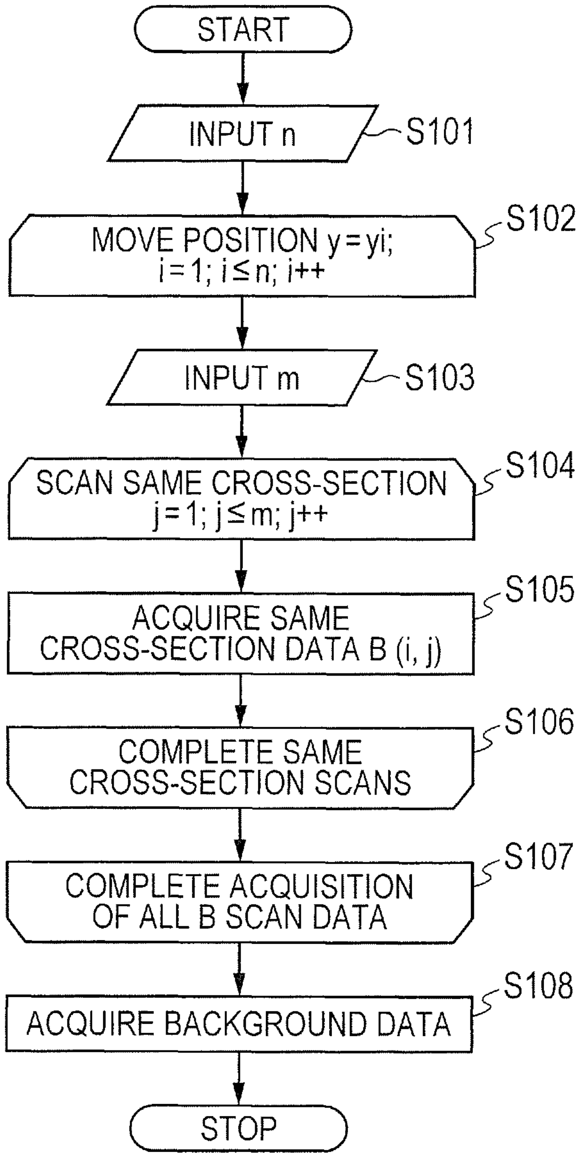
FIG. 4 is a flow chart for illustrating a procedure for acquiring a blood flow information cross-sectional image according to this embodiment.

Next, with reference to FIG. 4, description is given of a procedure of a specific process for acquiring the interference signal according to this embodiment.

In Step S101, the computer 40 defines n as a total number of an index i in a scan line yi illustrated in FIG. 3. After the definition, in Step S102, the computer 40 sets the index i of a position yi to 1. The OCT apparatus moves the radiating position of the measuring light to a position x1 at a position y1, and starts scanning with the measuring light in an X direction for acquiring p A scan signals successively from the position x1.

In Step S103, the computer 40 defines m as a total number of an index j in repeated B scans. After the definition, in Step S104, the computer 40 sets the index j of the repeated B scans to 1. After this setting, in Step S105, the computer 40 acquires a B scan signal in OCT. The differential detector 31 detects interference signals for each A scan, and the interference signals are stored in a memory of the computer 40 through the A/D converter 32. The computer 40 acquires p interference signals of the A scan, to thereby obtain the interference signals corresponding to one B scan.

In Step S106, the computer 40 returns the flow to Step S104 to determine whether or not the number of repetition times j of B scan has reached the predetermined number (m). That is, the computer 40 determines whether or not the B scan has been repeated m times at the position yi. In Step S104, the computer 40 repeatedly increments the index j of the repeated B scans until the index j matches the predetermined number m. After the increment, the flow further proceeds to Step S105 to repeat a loop for acquiring interference signals corresponding to one B scan on the same scan line again and returning to Step S104 from Step S106. When the index j reaches the predetermined number m, the flow proceeds to Step S107 via Step S106. Through the repetition of the B scans, m interference signal groups (data set groups) are obtained.

In Step S107, the computer 40 returns the flow to Step S102 to determine whether or not the number of lines i of the B scan has reached a predetermined number of measured lines (n). That is, the computer 40 determines whether or not the B scan has been carried out at all of the n y-positions designated within the scan area. In Step S102, the index i is repeatedly incremented until the index i matches the predetermined number of measured lines n. After the increment, the subsequent loop for returning from Step S107 to Step S102 is repeated. When the index i has reached the predetermined number of measured lines n, the flow proceeds to Step S108 via Step S107.

In Step S108, the OCT apparatus acquires, as background data, the output from the detector portion 30 under a state in which the measuring light is not received. When the background data is acquired, the computer 40 inserts the shutter 104 into the optical path of the measuring light for OCT, and executes data acquisition based on 100 A scans under a state in which the optical path is closed. The computer 40 averages and stores the data obtained based on the 100 A scans. In this embodiment, the number of times of measuring a background is set to 100, but is not limited thereto. After the above-mentioned steps are carried out, the flow for acquiring the interference signal is completed.

[Process for Extracting Interference Signal]

Next, description is given of a process for extracting the interference signal according to this embodiment. In this case, the extracting process represents a general process for extracting data from a plurality of pieces of data under a specific condition, for example, at a predetermined time interval. Specifically, an extraction interval used when data is partially extracted is fixed when the data is extracted from the data sets obtained from one B scan. In this embodiment, the fixed extraction interval is referred to as a longer sampling interval than a sampling interval used when the original data set is generated. However, the extracting process does not necessarily need to be performed at a fixed interval being a predetermined interval, and may be arbitrarily performed while an interval is changed. In addition, a range for extracting data may be an arbitrary region instead of the entire region of the interference signal. When a plurality of extraction patterns are used to obtain the plurality of data sets, data duplicate in individual extraction may be extracted.

In this case, the computer 40 functions as the data extracting unit configured to partially extract data included in the output data sets at the longer sampling interval than the interval for sampling the output light by the detector so as to generate a plurality of data sets. The computer 40 further forms the tomographic information based on the extracted and generated plurality of data sets. The tomographic information includes: the tomographic image and the blood flow information cross-sectional image of the eye to be inspected 120; and a luminance value and a motion amount used for generating those images.

This embodiment is described by taking an example of extracting and generating the interference signal group satisfying a specific condition from the interference signal group acquired based on a k-clock. In this embodiment, the number of images to be used for decorrelation calculation can be increased by the process for extracting the interference signal, and noise reduction can be achieved by the averaging process.

As described later, the extracting process may reduce the imaging depth range for OCT depending on its mode. An imaging depth range d for OCT depends on a minimum wavenumber interval δk for detecting the interference signal in principle, and is expressed by the following expression.

$$d = \frac{1}{4 * \delta k}$$

In a spectral domain method (hereinafter referred to as "SD method"), the minimum wavenumber interval δk depends on performance of a spectroscope and a resolution of the CCD sensor array, and the imaging depth range becomes deeper as the resolution becomes higher. Meanwhile, in a swept source method (hereinafter referred to as "SS method"), the minimum wavenumber interval δk depends on a clock signal synchronized with the wavenumber (hereinafter referred to as and "k-clock"), and δk becomes finer as the k-clock becomes higher in frequency, which can deepen the imaging depth range.

In this case, it is assumed that an OCT interference signal is subjected to a process for extracting the interference signal group existing at a predetermined clock signal interval. Specifically, for example, there is an interference signal group corresponding to clock signals c1, c2, c3, c4, c5, c6, . . . , c(n), c(n+1), c(n+2), . . . From such an interference signal group, an interference signal group of the clock signals c1, c4, c7, . . . , c(3n−2), . . . is extracted at a predetermined clock signal interval w=3. In this case, the minimum wavenumber interval δk becomes wider, and as a result, the imaging depth range d decreases in an inversely proportional relationship to the minimum wavenumber interval δk as expressed by the above-mentioned expression. Therefore, when the image is reconstructed after extracting the interference signals at the predetermined clock signal interval w, the imaging depth range of the tomographic image is reduced to 1/w.

Meanwhile, assuming that a coherence function is a Gaussian shape, a longitudinal resolution Δz for OCT is theoretically calculated by the following expression.

$$\Delta z = \frac{2\ln 2}{\pi} \cdot \frac{\lambda_0^2}{\Delta\lambda_{FWHM}}$$

where Λ0 represents a center wavelength of an irradiation light source, and ΔΛ represents a half-value width of a spectrum. The above-mentioned expression indicates that Λ0 or ΔΛ is hardly changed when the interference signal is extracted at the predetermined clock signal interval. Therefore, in the extracting process according to this embodiment, the imaging depth range (display range of a tomographic image in the depth direction) is reduced, while a longitudinal resolution (resolution of an individual tomographic image) is inhibited from dropping. This also inhibits the longitudinal resolution of each tomographic image from dropping even when a plurality of tomographic images are generated from the respective interference signal groups obtained by the extracting process.

It is known that, as described above, in OCTA, the imaging requires much time because the B scan is required to be performed on the same scan line a plurality of times and it is desired to make both the x-pitch and the y-pitch smaller than the beam spot diameter. Therefore, in OCTA, the scan area is preferred to be made narrower than general OCT imaging. In this case, when the scan area becomes narrower, the need for taking curvature of the fundus into consideration becomes lower, and hence a desired tomographic image is obtained even when the imaging depth range is reduced. That is, OCTA does not require as large an imaging depth range as the imaging depth range for obtaining the intensity image by general OCT. Therefore, as described above, an intended tomographic image is obtained even when a plurality of interference signal groups are extracted from an original interference signal group and the tomographic image having a smaller imaging depth range is generated from each of the interference signal groups.

When a plurality of tomographic images are obtained from the same scan line, for example, an averaging process or the like is performed on those images, to thereby effectively improve a signal noise ratio (SNR) of the blood flow information cross-sectional image. In particular, the SS method using a band having a center wavelength of 1 μm has a feature that the longitudinal resolution is about 10 μm, which is lower than in the SD method, while the imaging depth is deeper. Therefore, SS-OCT is suitable for a method of generating a plurality of interference signal groups by the extracting process to generate a large number of images having a small imaging depth range as in this embodiment.

Figure 5:
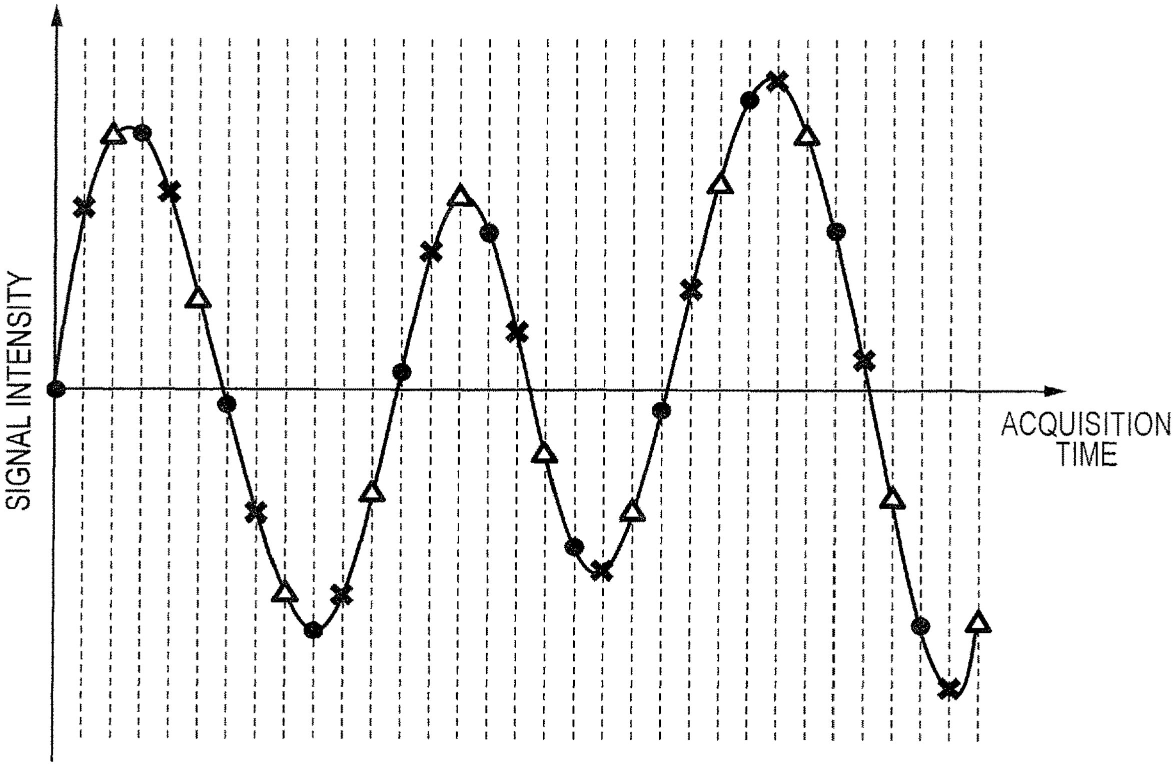
FIG. 5 is a graph for showing a method of extracting a signal at a predetermined interval.
Figure 6:
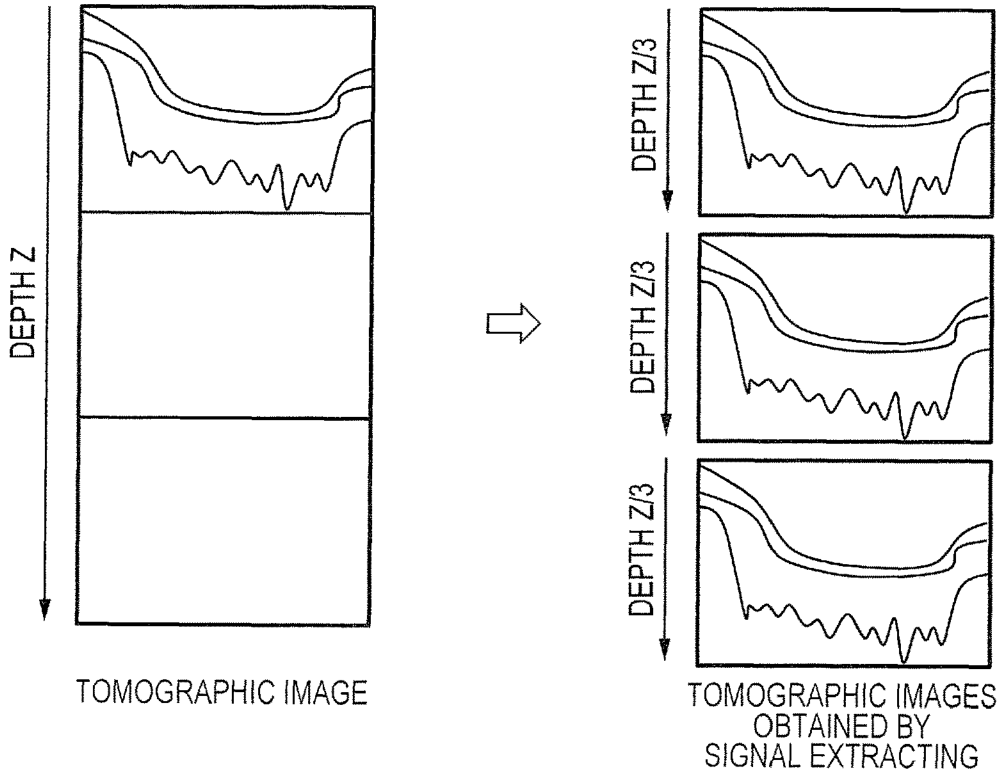
FIG. 6 is a diagram for illustrating a relationship between tomographic images obtained by signal extracting and their original tomographic image.

Now, an example of extracting the interference signal group from among the interference signal groups at the predetermined clock signal interval w=3 as in this embodiment is described specifically with reference to FIG. 5 and FIG. 6. The vertical dotted lines within FIG. 5 correspond to timings for emitting the k-clock signal, and each interval between the adjacent dotted lines represents the minimum wavenumber interval δk. In the general OCT imaging, the sampling of the interference light is performed at the minimum wavenumber interval δk. When the extraction is performed from among the interference signal groups at the predetermined clock signal interval w=3, the interference signal group is extracted at an interval being three times as large as the minimum wavenumber interval δk. That is, when the extraction performed from among data output from the detector portion 30 uses an interval for extracting every w-th piece of data among the output data as the longer sampling interval being an extraction condition, the number of interference signal groups being the plurality of data sets to be obtained is w (namely, 3).

In the case of FIG. 5, each of the interference signal groups having values respectively represented by the black circle marks, the X marks, and the white triangle marks is extracted. In more detail, the black circle mark represents an output value obtained from the sampled interference light corresponding to a clock signal satisfying the condition of being the (3×(n−1))-th (where n is an integer) clock signal. The X mark represents an output value obtained from the sampled interference light corresponding to a clock signal satisfying the condition of being the 1+3×(n−1)-th clock signal. The white triangle mark represents an output value obtained from the sampled interference light corresponding to a clock signal satisfying the condition of being the 2+3×(n−1)-th clock signal. From the three extracted interference signal groups, three tomographic images in total can be generated for each tomographic image as illustrated in FIG. 6. As described above, the minimum wavenumber interval δk for the interference signal used for generating each image in this case is three times as large as the minimum wavenumber interval δk used for obtaining an original tomographic image in the left half of FIG. 6. Therefore, the tomographic images generated from the three extracted interference signal groups are each an image having an imaging depth range of Z/3 compared with the original tomographic image having an imaging depth range of Z as illustrated in the right half of FIG. 6.

In this manner, when the imaging depth range becomes ⅓, it is conceivable that the tomographic image may be folded back at a lower edge depending on an acquisition position of the tomographic image, a degree of curvature of the retina for which the tomographic image has been generated, or the like. In this case, the fundus needs to be imaged again with the retinal layer being brought closer to the coherence gate to newly generate a plurality of tomographic images. That is, in order to handle an occurrence of such folding back, for example, the tomographic images generated from the interference signals obtained through the splitting may be displayed as the optical coherence tomographic image 209 on the imaging screen 200 illustrated in FIG. 2B, and the position of the coherence gate or the number of splitting may be adjusted so as to prevent the folding back. As described above, the adjustment of the coherence gate or the number of splitting may be manually performed by the examiner through use of the gate adjustment slider 207 or a splitting number setting unit (not shown). In another case, the adjustment may be automatically performed by the computer 40 based on the optical coherence tomographic image 209 depending on the imaging depth range, the measurement time, the wavelength range of the light source, or the like.

When a decorrelation between the individual interference signal groups to be used for obtaining the blood flow information is calculated, a decorrelation between the tomographic images in the same region which are scanned at a predetermined time interval Δt (between the interference signal groups obtained from the same scan lines at different times) is calculated. The decorrelation of the tomographic image acquired in the first A scan at a time t1 is to be calculated with respect to the tomographic image acquired in the second A scan at a time t2. In the same manner, the decorrelation of the tomographic image acquired in the second A scan at the time t2 is to be calculated with respect to the tomographic image acquired in the third A scan at a time t3 excluding the tomographic image acquired in the first A scan.

Figure 7:
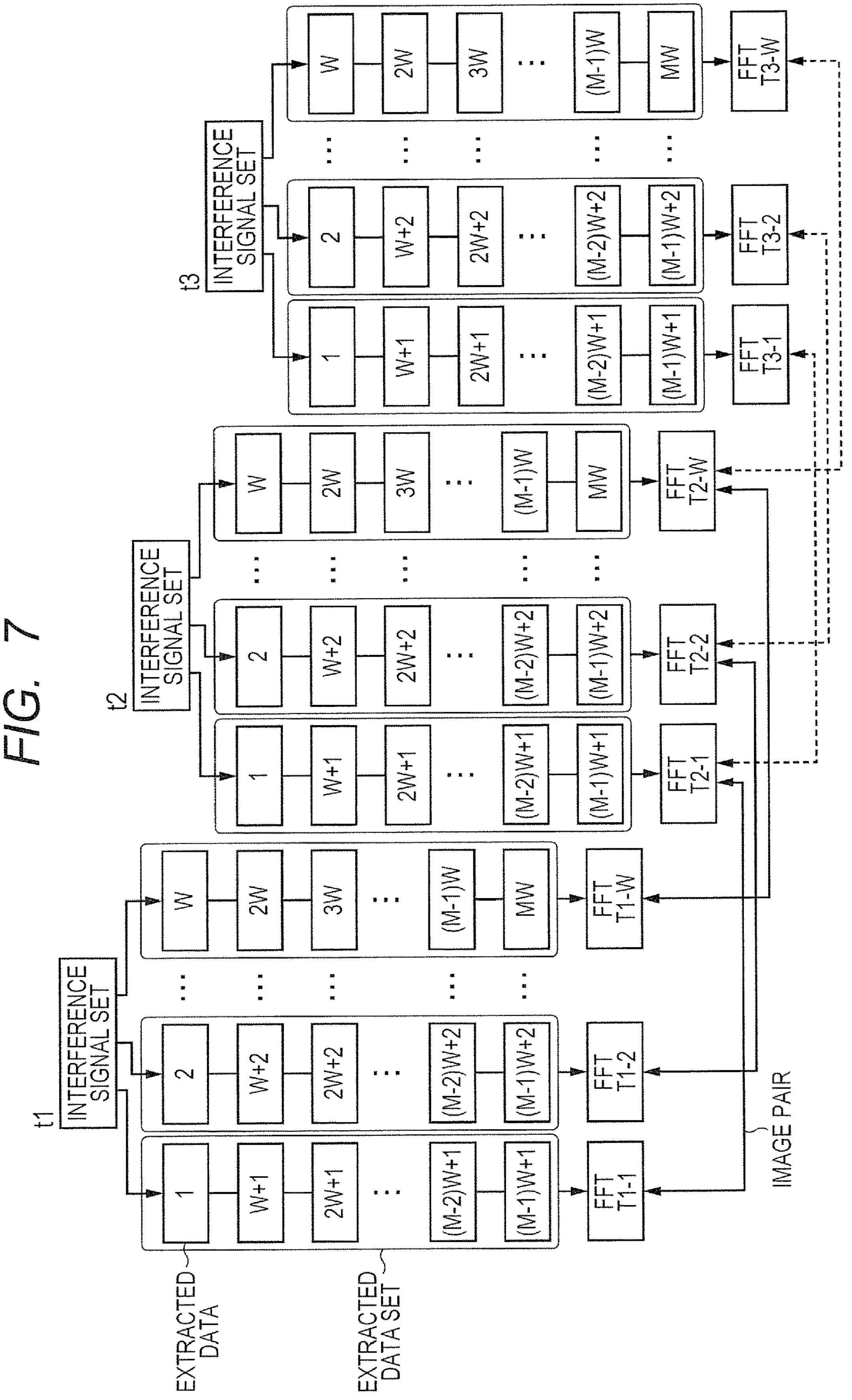
FIG. 7 is a diagram for illustrating relationships among respective interference signal groups used for calculating a decorrelation between interference signals extracted at the predetermined interval.

Therefore, when the predetermined interval for the splitting is set to w times as large as the sampling interval and the number of repeated scans for the same region is set to m, w×(m−1) decorrelation images in total can be obtained. FIG. 7 is an explanatory diagram for illustrating the interference signal groups (tomographic images) obtained at different times, the extracted interference signal groups (tomographic images), and how to perform extraction from those interference signal groups in order to obtain the decorrelation image. In this embodiment, the predetermined interval for the splitting is set to three times (w=3) as large as the sampling interval, and the number of repeated scans for the same region is set to 3 (m=3). In FIG. 7, a combination for decorrelation image generation executed in this embodiment in the above-mentioned case is exemplified. In the example illustrated in FIG. 7, assuming that w=3, three interference signal sets (for example, FFT T1-1, FFT T1-2, and FFT T1-3) are extracted from each of the interference signal sets obtained at the times t1, t2, and t3. It is possible to obtain 3×2=6 decorrelation images between the interference signal set obtained at the time t1 and the interference signal set obtained at the time t2. The extracted interference signal sets that are connected on a one-to-one basis by the arrows in FIG. 7 indicate how to combine the interference signal sets in order to obtain the decorrelation image.

In addition, in the case of SS-OCT, there are several methods of increasing the imaging depth. Specific examples of the methods include a doubling process for an interleaving function of a DAQ board or the k-clock and rescaling of a wavelength based on a signal process. It is possible to obtain a deeper tomographic image by utilizing those methods. It is possible to extract the interference signals by splitting the interference signal group for obtaining such an image at a predetermined larger interval, and to further increase the number of tomographic images. As a result, it is possible to generate the blood flow information cross-sectional image having a higher SNR.

In this case, it is desired that the coherence gate position be adjusted so as to fall within a range of 2.5 mm from the retina. This is because the above-mentioned numerical value is statistically considered as such a maximum allowable range of the coherence gate position as to inhibit the retina from being folded back at the lower edge of the tomographic image. Therefore, for example, an imaging depth range of 5 mm is required to perform the extracting process at a predetermined interval set to w=2 times as large as the sampling interval. However, the imaging depth range can also be set to 2.5 mm when the method of doubling the imaging depth by doubling the interleaving function or the clock, which is described later in detail, is taken into consideration.

Figure 8:
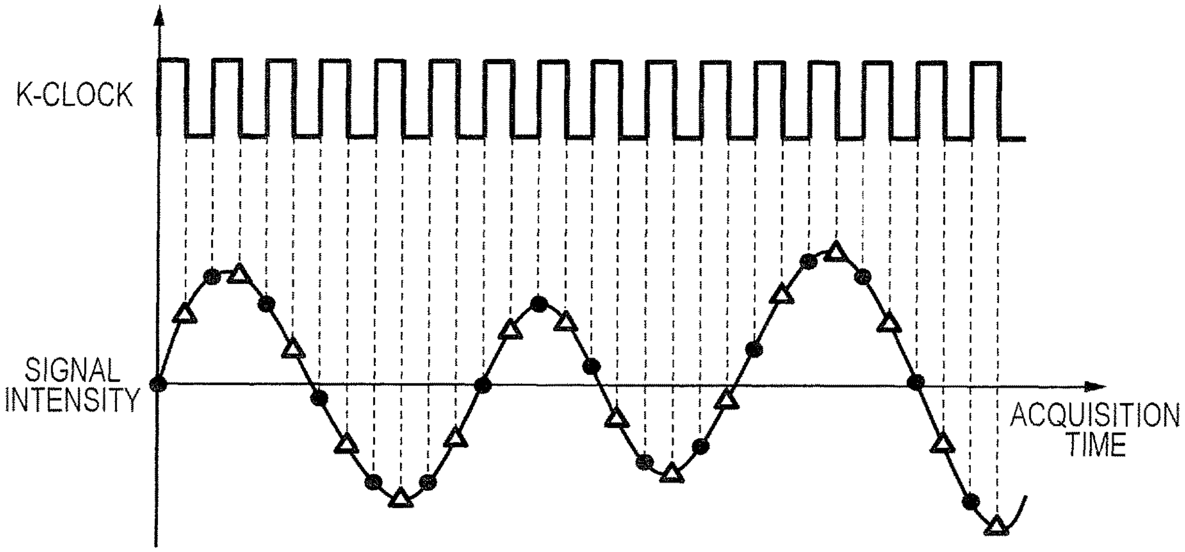
FIG. 8 is a graph for showing a case of increasing the signals in number through use of an interleaving function and extracting an interference signal group from the signals.

In addition, for example, as shown in FIG. 8, when the number of sampling points are doubled through use of the interleaving function of a DAQ, the decorrelation image can also be calculated by using the following method as a process equivalent to the process for extracting the interference signal group. That is, when the interference signal is acquired based on the k-clock, in general, an interference signal group A (corresponding to values indicated by the black circle marks in FIG. 8) formed of only rising edges of the clock is acquired. When the interleaving function is used, not only the interference signal group A but also an interference signal group B (corresponding to values indicated by the white triangle marks in FIG. 8) formed of falling edges of the clock are separately acquired.

In this case, when the decorrelation is calculated, as described above, the decorrelation between the interference signal groups A or between the interference signal groups B is calculated from among the interference signal groups in the same region which are scanned at the predetermined time interval Δt. The tomographic image before the extraction in this case is generated from interference signals A formed of only the rising edges of the clock, interference signals B formed of only the falling edges of the clock, or all of the interference signals formed of both the rising edges of the clock and the falling edges of the clock. The above-mentioned process for doubling the number of pieces of data to be output is executed by the detector portion 30 and the computer 40. The extracting process is executed for the data set generated by the doubling. The interference signal groups obtained by the above-mentioned process have the number of pieces of data increased without changing a measuring range, and hence it is possible to split the interference signal at a predetermined larger interval. Therefore, the number of tomographic images can be further increased, and it is possible to generate the blood flow information cross-sectional image having a higher SNR.

[Signal Process Procedure]

Figure 9:
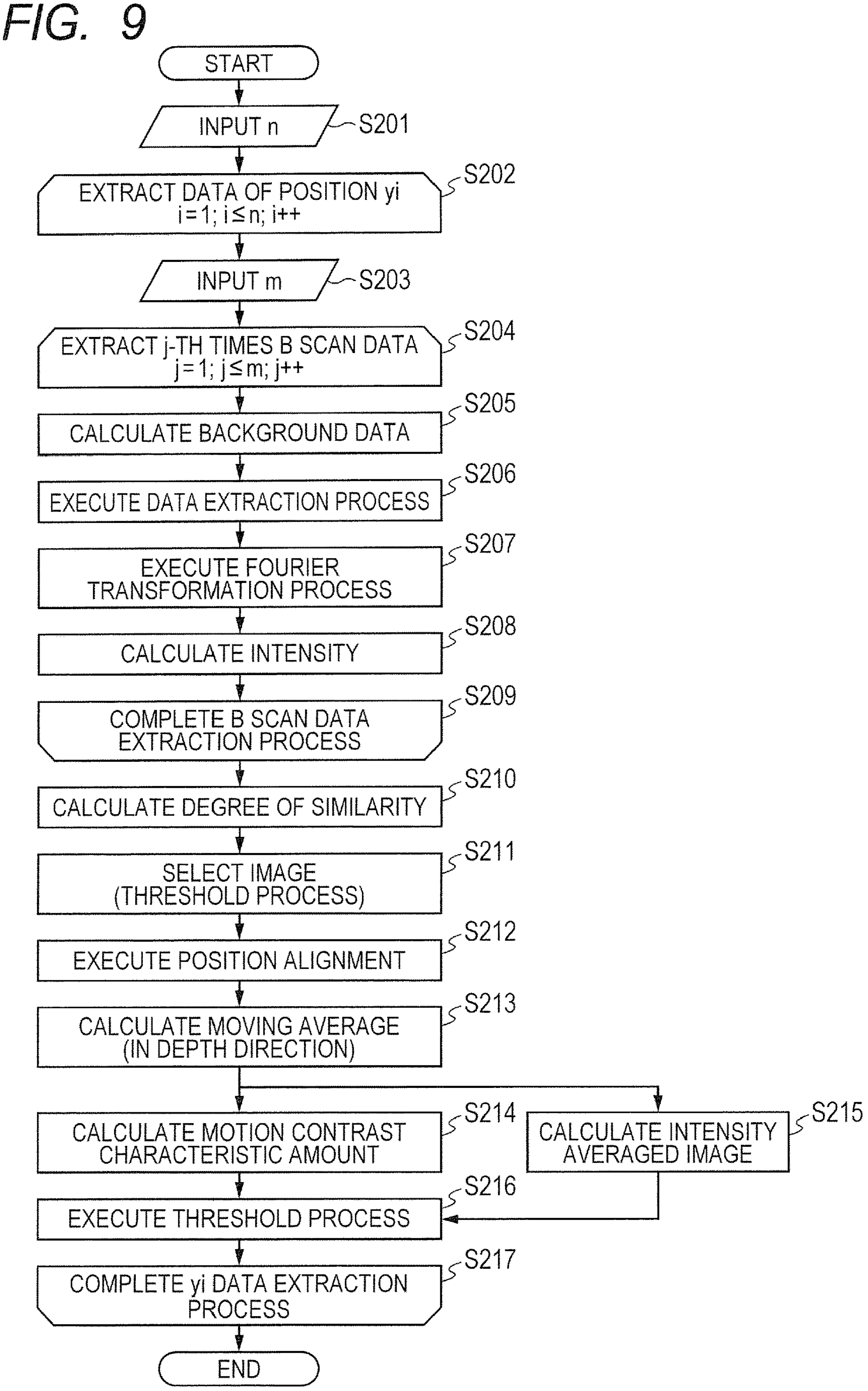
FIG. 9 is a flow chart for illustrating a procedure for a signal process according to this embodiment.

Next, with reference to FIG. 9, description is given of a procedure of a specific process according to this embodiment. FIG. 9 is a flow chart for illustrating the procedure performed until three-dimensional blood flow information is output as a result of performing the signal process by the computer 40 receiving the input of the interference signal.

In this flow chart, first in Step S201, the computer 40 defines the number of pieces of data n as a total number of a position yi in the scan line illustrated in FIG. 3. After the definition, the OCT apparatus executes the extraction of B scan data on the fundus with the measuring light at the position y1. In Step S202, the computer 40 instructs the extraction of the interference signal group (hereinafter referred to as "B scan data") corresponding to one frame obtained by the B scan at the position y1.

In Step S203, the computer 40 defines the total number of repetition times m in the repeated B scans. In Step S204, the computer 40 sets the number of repeated B scans j to 1, and instructs the extraction of the first B scan data. In Step S205, the computer 40 subtracts the background data acquired by the OCT apparatus in the above-mentioned procedure for acquiring the interference signal from the acquired interference signal group. In Step S206, the computer 40 subjects the original interference signal group from which the background data has been subtracted to the extracting process at the above-mentioned predetermined interval set to w times as large as the sampling interval to extract a plurality of interference signal groups.

In Step S207, the computer 40 executes a Fourier transformation process on each of w interference signal groups generated by the extracting process. In this embodiment, a fast Fourier transformation (FFT) is employed as the Fourier transformation process. A zero padding process may be executed before the Fourier transformation process to increase the interference signals. The execution of the zero padding process increases gradation after the Fourier transformation process, and enables improvement in position alignment accuracy in Step S212, which is described later.

In Step S208, the computer 40 calculates an absolute value of a complex signal obtained by the Fourier transformation process executed in Step S207. The absolute value is used as the intensity of each of the w tomographic images obtained from the relevant B scan data. In Step S209, the computer 40 returns the flow to Step S204, and in Step S204, determines whether or not the index j of the repeated B scans has reached a predetermined number (m). That is, it is determined whether or not the calculation of the intensities of the w tomographic images for each B scan data at the position yi has been repeated m times. When the predetermined number m has not been reached, the index j is incremented, and the process from Step S205 to Step S208 is further repeated. That is, after that, the process for extracting the repeated B scan data at the same Y-position and the calculation of the intensity based on each of the extracted interference signal groups up to Step S208 are repeated. When j has reached the predetermined number m, the flow proceeds to Step S210 via Step S209. That is, the data set output from the detector portion 30 and processed by the computer 40 are a plurality of data sets obtained by the data extracting unit performing the process for extraction and generation on each of m data sets obtained in the same scan line.

In Step S210, the computer 40 calculates a degree of similarity between images among the frames (tomographic image groups) obtained from m×w data sets obtained by the repeated B scans and the extracting process at a given position yi. Specifically, the computer 40 selects one frame under an arbitrary extraction condition from among m×w frames of tomographic images (B-scanned data) as a template, and calculates a correlation value with respect to one image under the corresponding extraction condition among the remaining (m−1)×w frames of images. The interference signal is split by the number of splitting w, and hence there are m×w frames of images, but a pair of tomographic images acquired at the same time is not used for the calculation of the correlation value. The degree of similarity between the images is calculated from among the frames generated by the extraction from m−1 interference signal groups acquired by the imaging at different times. Therefore, the correlation value is calculated in association with each of the m−1 images.

In Step S211, the computer 40 selects an image having a high correlation equal to or higher than a fixed threshold value from among the correlation values calculated in Step S210. At this time, for each image, the remaining w−1 images acquired at the same time are each selected as the image having a high correlation under the corresponding extraction condition in the same manner. The threshold value can be arbitrarily set so as to avoid use of a frame having a lowered correlation in terms of the entire image due to blinking or involuntary eye movement during fixation of the subject to be examined.

As described above, OCTA is a technology for acquiring a contrast between the tissue involving flowing (for example, blood) and the tissue involving no flowing among tissues of the eye to be inspected as a motion contrast characteristic value by distinguishing the two tissues based on the correlation value between their images. That is, the issue involving flowing is extracted on the assumption that the tissue involving no flowing exhibits a high correlation between the images. Therefore, in a case where the correlation is low in terms of the entire image, when the motion contrast characteristic amount is calculated, it may be erroneously determined that all pixels exhibit time modulation and the entire image indicates the tissue involving flowing. In order to avoid such a detection error, in Step S211, the image having a low correlation in terms of the entire image is excluded in advance, and only the image having a high correlation is selected. As a result of image selection, m frames of images acquired at the same position yi are appropriately selected to become r frames of the images, where r takes a value within a range of $1 \le r \le m$.

In Step S212, the computer 40 performs position alignment of the frames determined to have a high correlation as the interference signal group under the corresponding extraction condition among the extracted w interference signal groups within the repeated B scan data at a given position yi. The position alignment is not performed for the tomographic images acquired at the same time, that is, the tomographic images obtained from the interference signal groups extracted from the same B scan data.

Specifically, the computer 40 first selects one arbitrary frame among the m×w frames as a template. To select the frame as the template, the correlations may be calculated for every combination to obtain a sum of the correlation values for each frame, and the frame having the largest sum may be selected. In this embodiment, as illustrated in FIG. 7, the frames having the correlation to be calculated in this case are limited to the tomographic images generated from the interference signal groups extracted under the same extraction condition as the extraction condition for the one arbitrary frame to be selected as the template.

Subsequently, the template is compared with each frame to obtain a positional displacement amount ($\delta X, \delta Y, \delta\theta$). Specifically, a normalized cross-correlation (NCC) being an index representing a degree of similarity is calculated while changing the position and the angle of the template image, and a difference in image position when the value becomes maximal is obtained as a positional displacement amount. In this disclosure, various changes can be made to the index representing the degree of similarity as long as the index is a scale representing the degree of similarity between characteristics of the images in the template and the frame. For example, a sum of absolute difference (SAD), a sum of squared difference (SSD), a zero-means normalized cross-correlation (ZNCC), a phase only correlation (POC), or a rotation invariant phase only correlation (RIPOC) may be used.

Subsequently, the computer 40 applies position correction to (r−1)×w frames other than the template based on the positional displacement amount ($\delta X, \delta Y, \delta\theta$) to perform the position alignment of the frames. The execution of this step is skipped when r is 1.

In Step S213, the computer 40 calculates a moving average in the depth direction as necessary. The moving average is calculated for every pixel of each frame with an arbitrary width in the depth direction for each pixel. In this process, which is particularly effective for an image exhibiting large movement in a Z-axis direction, it is possible to lower a detection sensitivity for the decorrelation derived from the axial-direction movement of an object to be inspected that is not derived from the blood flow, and as a result, it is possible to improve an extraction sensitivity for the blood flow.

After the above-mentioned process is completed, each interference signal group is brought into a state that facilitates the extraction of the motion contrast derived from the blood flow. In Step S214, the computer 40 calculates the motion contrast characteristic amount based on each tomographic image subjected to the position alignment or the like. In this embodiment, the computer 40 calculates a dispersion value for each of the pixels at the same position between r frames of intensity images subjected to the moving average process in Step S213, and sets the dispersion value as the motion contrast characteristic amount. There are various methods of calculating the motion contrast characteristic amount, and in the embodiment of the present disclosure, any index representing a change in luminance value of each pixel of a plurality of B scan images at the same Y-position can be employed as a type of the motion contrast characteristic amount.

A different process is performed when r=1, that is, when the correlation in terms of the entire image is low due to influence of blinking or involuntary eye movement during fixation and the motion contrast characteristic amount cannot be calculated at the same position yi. For example, the step may be completed by setting the characteristic amount to 0, or when the motion contrast characteristic amount is obtained from a preceding image yi−1 and a succeeding image yi+1, the value may be interpolated from the preceding and succeeding dispersion values.

Further, in Step S215 simultaneously with Step S214, the computer 40 averages the intensity images subjected to the moving average process in Step S213 to generate an intensity averaged image. In Step S216, the computer 40 executes a threshold process for the motion contrast characteristic amount output in Step S214. The computer 40 extracts an area in which only random noise is displayed in a noise floor from the intensity averaged image output in Step S215, and calculates a standard deviation σ to set "(averaged luminance of noise floor)+2σ" as the threshold value. The computer 40 sets the value of the motion contrast characteristic amount having each intensity within a range equal to or smaller than the above-mentioned threshold value to 0. By the threshold process of Step S216, it is possible to remove the motion contrast derived from a change in intensity due to the random noise, to thereby reduce noise.

As the threshold value becomes smaller, a detection sensitivity for the motion contrast increases, and noise components also increase. In contrast, as the threshold value becomes larger, the noise components decrease, but the detection sensitivity for the motion contrast is lowered. In view of this, the threshold value is set to "(averaged luminance of noise floor)+2σ" in this embodiment, but the threshold value is not limited thereto.

In Step S217, the computer 40 returns the flow to Step S202 to determine whether or not the index i of the scanning position yi of the B scan has reached a predetermined number (n). That is, the calculation of image correlation, the image selection, the position alignment, the intensity image averaging calculation, the calculation of the motion contrast characteristic amount, and the threshold process have been executed at all of the n Y-positions. When the predetermined number n has not been reached, the index i is incremented, and the process from Step S203 to Step S216 at the subsequent scan positions is repeated. When the predetermined number n has been reached, the flow proceeds via Step S217 to complete the signal process flow. When Step S217 is completed, the intensity averaged images and three-dimensional volume data (three-dimensional blood flow information) on the motion contrast characteristic amounts of the B scan images at all of the Y-positions have been acquired.

That is, in the above-mentioned embodiment, the plurality of tomographic images are generated by a unit configured to generate a tomographic image based on each of the plurality of data sets generated by the extraction. The computer 40 functions as the arithmetic operation unit to perform a correlation operation between the tomographic images to acquire the blood flow information. As described above, according to this embodiment, it is possible to provide the imaging apparatus configured to generate three-dimensional blood flow information with high resolution and high sensitivity without extending the measurement time.

The image including the tomographic image generated from the tomographic information on the eye to be inspected 120, which is described above with reference to the example illustrated in FIG. 2A or FIG. 2B, is displayed by the display portion 70 in response to an instruction issued by the computer 40 functioning as a display control unit. By the above-mentioned signal process, the computer 40 can generate an image having a large imaging depth range being a first imaging depth range and an image having a small imaging depth range being a second imaging depth range narrower than the first imaging depth range. The computer 40 further selects which of those images is to be displayed based on an instruction from the examiner or the like or on the step of, for example, displaying an adjustment instruction screen for the coherence gate position, and displays the selected image on the display portion 70.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

The present disclosure is not limited to the above-mentioned embodiment, and may be conducted with various changes and modifications within the scope that does not depart from the gist of the present disclosure. For example, the description of the above-mentioned embodiment is directed to the case where an object to be inspected is an eye, but the present disclosure may be applied to an object to be inspected other than the eye, for example, skin or an organ. In this case, the present disclosure has a mode of an image pickup apparatus as medical equipment other than an ophthalmologic apparatus, for example, an endoscope. Accordingly, it is desired that the present disclosure be grasped as an image pickup apparatus exemplified by the ophthalmologic apparatus, which is configured to pick up an image of an object to be inspected, and that the eye to be inspected be grasped as one mode of the object to be inspected.

Further, the case of acquiring the blood flow information is described in the above-mentioned example, but the present disclosure is not limited thereto. For example, the forming unit may be configured to form an averaged image by averaging a plurality of interference signal groups obtained as shown in FIG. 5.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-065982, filed Mar. 29, 2016, which is hereby incorporated by reference herein in its entirety.

What is claimed is:

1. An information processing apparatus comprising:

a data extracting unit configured to partially extract, from an output from a sampling unit which samples interference light between (a) return light from an object to be inspected which is irradiated with measuring light and (b) reference light corresponding to the measuring light, A-scan data corresponding to a longer sampling interval than an interval for sampling the interference light by the sampling unit so as to generate A-scan data sets each of which is different from others of the A-scan data sets;

a generating unit configured to generate (a) first tomographic images regarding first B-scan data sets obtained at a first time and (b) second tomographic images regarding second B-scan data sets obtained at a second time different from the first time, the first B-scan data sets and the second B-scan data sets being B-scan data sets corresponding to the generated A-scan data sets, wherein B-scan data of the first B-scan data sets and of the second B-scan data sets are obtained by using A-scan data sets obtained by scanning the object with the measuring light;

a position alignment unit configured to perform a position alignment between at least one of the first tomographic images and at least one of the second tomographic images; and a forming unit configured to form tomographic information of the object to be inspected by using tomographic images obtained by performing the position alignment.

2. An information processing apparatus according to claim 1, wherein the forming unit is configured to form as the tomographic information, by performing a calculation regarding a correlation between the tomographic images obtained by performing the position alignment, blood flow information.

3. An information processing apparatus according to claim 1, wherein the forming unit is configured to form as the tomographic information, by averaging respective pixel values of the tomographic images obtained by performing the position alignment, an averaged image.

4. An information processing apparatus according to claim 1, wherein the forming unit is configured to form as the tomographic information, by performing a calculation regarding a correlation between the tomographic images obtained by performing the position alignment, motion contrast data.

5. An information processing apparatus according to claim 1, wherein the longer sampling interval used to partially extract the data by the data extracting unit is fixed when the data is extracted from the output.

6. An information processing apparatus according to claim 5, wherein the longer sampling interval comprises an interval for extracting every w-th piece of data included in the output from the sampling unit, where w represents a number of the A-scan data sets.

7. An information processing apparatus according to claim 1, wherein:

the output from the sampling unit comprises m outputs obtained by scanning the object to be inspected in the same scan line with the measuring light m times; and the data extracting unit is configured to generate the A-scan data sets from each of the m outputs.

8. An information processing apparatus according to claim 1, wherein:

the measuring light and the reference light are emitted from a light source being a wavelength-sweep light source capable of sweeping an optical wavelength over time; and the sampling unit is configured to sample the interference light at a predetermined equal wavenumber interval based on a sample clock output from a clock generating unit.

9. An information processing apparatus according to claim 8, wherein the sampling unit is configured to perform signal processing for doubling a number of pieces of data included in the output.

10. An information processing apparatus according to claim 1, wherein:

the sampling unit comprises: a spectroscopic unit configured to separate the interference light into spectral components; and light-receiving elements configured to receive the spectral components; and the sampling unit is configured to sample the interference light at a predetermined equal wavenumber interval based on outputs from the light-receiving elements.

11. An information processing apparatus according to claim 1, further comprising a display control unit configured to display on a display portion a tomographic image generated from the tomographic information on the object to be inspected, wherein:

the forming unit is capable of generating the tomographic image having a first imaging depth range based on the output and the tomographic image having a second imaging depth range smaller than the first imaging depth range based on the generated A-scan data sets; and the display control unit is configured to select any one of the tomographic image having the first imaging depth range and the tomographic image having the second imaging depth range, and to display the selected tomographic image on the display portion.

12. An information processing apparatus according to claim 11, wherein:

the object to be inspected comprises a fundus of an eye to be inspected;

the tomographic image having the first imaging depth range comprises a tomographic image having a depth range equal to or larger than 4.0 mm; and the tomographic image having the second imaging depth range comprises a tomographic image having a depth range smaller than 4.0 mm.

13. An information processing apparatus according to claim 11, wherein the extracted A-scan data sets for generating the tomographic image having the second imaging depth range are based on output light obtained under a condition that a scan angle range of the measuring light is smaller than 47°.

14. An information processing apparatus according to claim 11, wherein the data extracting unit is configured to extract the A-scan data sets for generating the tomographic image having the second imaging depth range when a scan angle range of the measuring light is smaller than 47°.

15. An information processing apparatus according to claim 1, wherein:

the object to be inspected comprises a fundus of the eye to be inspected;

the information processing apparatus further comprises an imaging range setting unit configured to set a predetermined range of the fundus to be scanned with the measuring light in a two-dimensional scan pattern formed of a predetermined number of scan lines;

the imaging range setting unit is capable of changing a scan angle of the measuring light between a first imaging range equal to or larger than 47° and a second imaging range smaller than 47°; and the sampling unit is configured to obtain the tomographic information in an imaging depth range equal to or larger than 4.0 mm inside an eyeball of the eye to be inspected.

16. A control method for an information processing apparatus, the control method comprising:

partially extracting, from an output from a sampling unit which samples interference light between (a) return light from an object to be inspected which is irradiated with measuring light and (b) reference light corresponding to the measuring light, A-scan data corresponding to a longer sampling interval than an interval for sampling the interference light by the sampling unit so as to generate A-scan data sets each of which is different from others of the A-scan data sets;

generating (a) first tomographic images regarding first B-scan data sets obtained at a first time and (b) second tomographic images regarding second B-scan data sets obtained at a second time different from the first time, the first B-scan data sets and the second B-scan data sets being B-scan data sets corresponding to the generated A-scan data sets, wherein B-scan data of the first B-scan data sets and of the second B-scan data sets are obtained by using A-scan data sets obtained by scanning the object with the measuring light;

performing a position alignment between at least one of the first tomographic images and at least one of the second tomographic images; and forming tomographic information of the object to be inspected by using tomographic images obtained by performing the position alignment.

17. A non-transitory computer-readable storage medium having stored thereon a program for causing a computer to execute the control method of claim 16.

18. An information processing apparatus according to claim 1, further comprising a setting unit for setting a predetermined area of the object to be inspected, the predetermined area being scanned with the measuring light, by a two-dimensional scan pattern formed by a predetermined number of scan lines, wherein the setting unit is capable of changing a scan angle of the measuring light between a first imaging range equal to or larger than 47° and a second imaging range smaller than 47°.

19. An information processing apparatus according to claim 1, further comprising a setting unit for setting a predetermined area of the object to be inspected, the predetermined area being scanned with the measuring light, by a two-dimensional scan pattern formed by a predetermined number of scan lines, wherein the setting unit is capable of changing a scan angle of the measuring light between a first image acquiring area and a second image acquiring area different from the first image acquiring area.

20. An apparatus comprising:

a sampling unit configured to sample interference light between (a) return light from an object to be inspected which has been scanned with measuring light and (b) reference light corresponding to the measuring light;

a data extracting unit configured to partially extract, from an output from the sampling unit, data included in the output at a longer sampling interval than an interval for sampling the interference light by the sampling unit so as to generate data sets;

a forming unit configured to form tomographic information on the object to be inspected based on the generated data sets; and a setting unit for setting a predetermined area of the object to be inspected, the predetermined area being scanned with the measuring light, by a two-dimensional scan pattern formed by a predetermined number of scan lines, wherein the setting unit is capable of changing a scan angle of the measuring light between a first imaging range equal to or larger than 47° and a second imaging range smaller than 47°.

21. A control method for an apparatus, the control method comprising:

sampling, by a sampling unit, interference light between (a) return light from an object to be inspected which has been scanned with measuring light and (b) reference light corresponding to the measuring light;

partially extracting, from an output from the sampling unit, data included in the output at a longer sampling interval than an interval for sampling the interference light by the sampling unit so as to generate data sets;

forming tomographic information on the object to be inspected based on the generated data sets; and setting, by a setting unit, a predetermined area of the object to be inspected, the predetermined area being scanned with the measuring light by a two-dimensional scan pattern formed by a predetermined number of scan lines, wherein the setting unit is capable of changing a scan angle of the measuring light between a first imaging range equal to or larger than 47° and a second imaging range smaller than 47°.

22. A non-transitory computer-readable storage medium having stored thereon a program for causing a computer to execute the control method of claim 21.

23. An information processing apparatus according to claim 1, wherein the A-scan data sets are extracted from one A-scan data obtained from the interference light sampled by the sampling unit, and wherein each of the first tomographic images and the second tomographic images is generated using A scan data sets corresponding to the B-scan data obtained by scanning the object to be inspected with the measuring light.

24. An image processing apparatus comprising:

a data extracting unit configured to partially extract, from an output from a sampling unit which samples interference light between (a) return light from an object to be inspected which is irradiated with measuring light and (b) reference light corresponding to the measuring light, A-scan data corresponding to a longer sampling interval than an interval for sampling the interference light by the sampling unit so as to generate A-scan data sets each of which is different from others of the A-scan data sets; and a generating unit configured to generate tomographic images regarding B-scan data sets corresponding to the generated A-scan data sets, wherein B-scan data of the B-scan data sets is obtained by using A-scan data sets obtained by scanning the object with the measuring light.

25. An image processing apparatus according to claim 24, further comprising a forming unit configured to form tomographic information of the object to be inspected by using tomographic images obtained by performing the position alignment.

26. An image processing apparatus according to claim 25, wherein the forming unit is configured to form as the tomographic information, by performing a calculation regarding a correlation between the tomographic images obtained by performing the position alignment, blood flow information.

27. An image processing apparatus according to claim 25, wherein the forming unit is configured to form as the tomographic information, by averaging respective pixel values of the tomographic images obtained by performing the position alignment, an averaged image.

28. An image processing apparatus according to claim 25, wherein the forming unit is configured to form as the tomographic information, by performing a calculation regarding a correlation between the tomographic images obtained by performing the position alignment, motion contrast data.

29. A control method for an image processing apparatus, the control method comprising:

partially extracting, from an output from a sampling unit which samples interference light between (a) return light from an object to be inspected which is irradiated with measuring light and (b) reference light corresponding to the measuring light, A-scan data corresponding to a longer sampling interval than an interval for sampling the interference light by the sampling unit so as to generate A-scan data sets each of which is different from others of the A-scan data sets; and generating tomographic images regarding B-scan data sets corresponding to the generated A-scan data sets, wherein B-scan data of the B-scan data sets is obtained by using A-scan data sets obtained by scanning the object with the measuring light.

30. A non-transitory computer-readable storage medium having stored thereon a program for causing a computer to execute the control method of claim 29.

31. An image processing apparatus according to claim 24, wherein the sampling unit is configured to sample an interference signal obtained by detecting the interference light.

32. An apparatus according to claim 20, wherein the forming unit is configured to form as the tomographic information, by averaging respective pixel values of the tomographic images obtained by performing the position alignment, an averaged image.

33. An information processing apparatus according to claim 1, wherein the sampling unit is configured to sample an interference signal obtained by detecting the interference light.

* * * * *